United States Patent
Salvi et al.

(10) Patent No.: US 11,574,739 B2
(45) Date of Patent: Feb. 7, 2023

(54) SYSTEMS AND METHODS FOR FORMULATING PERSONALIZED SKINCARE PRODUCTS

(71) Applicant: Atolla Skin Health, Inc., Belmont, MA (US)

(72) Inventors: Sid Salvi, Cambridge, MA (US); Meghan Maupin, Belmont, MA (US); Nava Haghighi, Los Angeles, CA (US)

(73) Assignee: Function, Inc., Paxinos, PA (US)

( * ) Notice: Subject to any disclaimer, the term of this patent is extended or adjusted under 35 U.S.C. 154(b) by 230 days.

(21) Appl. No.: 16/710,272

(22) Filed: Dec. 11, 2019

(65) Prior Publication Data
US 2020/0111577 A1 Apr. 9, 2020

Related U.S. Application Data

(63) Continuation of application No. 16/259,831, filed on Jan. 28, 2019, now Pat. No. 10,546,658.
(Continued)

(51) Int. Cl.
*G16H 50/30* (2018.01)
*G16H 20/10* (2018.01)
(Continued)

(52) U.S. Cl.
CPC ............. *G16H 50/30* (2018.01); *A45D 44/00* (2013.01); *A61B 5/0077* (2013.01); *G06N 5/04* (2013.01);
(Continued)

(58) Field of Classification Search
CPC ........ G16H 50/20; G16H 50/30; G16H 10/60; G16H 20/10; G16H 30/40; G06N 5/04; A61B 50/0077; A45D 44/00
See application file for complete search history.

(56) References Cited

U.S. PATENT DOCUMENTS 5,789,191 A 8/1998 Mayer et al.
6,068,848 A 5/2000 Gubernick et al.
(Continued)

FOREIGN PATENT DOCUMENTS

EP 2389573 A2 11/2011
WO 2001018674 A2 3/2001
(Continued)

OTHER PUBLICATIONS

Adamson, Adewole, "Machine Learning and Health Care Disparities in Dermatology," JAMA Dermatology, Nov. 2018, vol. 154, No. 11 (Year: 2018).*
(Continued)

*Primary Examiner* — John P Go
(74) *Attorney, Agent, or Firm* — Cesari & McKenna, LLP

(57) ABSTRACT

Systems and methods for formulating a personalized skincare product for a user. Data inputs reflecting dermal information of the user (e.g., hydration level measurements, oil level measurements, and a photograph of the user's skin reflecting a set of skin concerns) are collected by a computing device and used to determine a set of normalized scores. A skin health data set is generated based on the normalized scores and stored in memory. A skin health metric is determined based on the skin health data set and is stored in memory. The computing device determines, using a machine learning framework, one or more first skincare product formulations based on the user skin health data set. The formulation(s) can be used to manufacture one or more customized skincare products for the user and can be iteratively refined over time, e.g., by collecting additional data from the user over time.

13 Claims, 15 Drawing Sheets

Related U.S. Application Data

(60) Provisional application No. 62/623,207, filed on Jan. 29, 2018.

(51) Int. Cl.
  *G16H 10/60* (2018.01)
  *G16H 50/20* (2018.01)
  *G16H 30/40* (2018.01)
  *A45D 44/00* (2006.01)
  *A61B 5/00* (2006.01)
  *G06N 5/04* (2006.01)

(52) U.S. Cl.
  CPC ............ *G16H 10/60* (2018.01); *G16H 20/10* (2018.01); *G16H 30/40* (2018.01); *G16H 50/20* (2018.01); *A45D 2044/007* (2013.01)

(56) References Cited

U.S. PATENT DOCUMENTS

| | | |
|---|---|---|
| 6,121,243 A | 9/2000 | Lanzendörfer et al. |
| 6,358,539 B1 | 3/2002 | Murad |
| 6,596,761 B2 | 7/2003 | Lanzendörfer et al. |
| 6,673,756 B2 | 1/2004 | Sonnenberg et al. |
| 6,923,975 B2 | 8/2005 | Aronson et al. |
| 7,349,857 B2 | 3/2008 | Manzo |
| 7,477,767 B2 | 1/2009 | Chhibber et al. |
| 7,738,032 B2 | 6/2010 | Kollias et al. |
| 8,026,942 B2 | 9/2011 | Payonk et al. |
| 8,131,029 B2 | 3/2012 | Chhibber et al. |
| 8,155,413 B2 | 4/2012 | Chhibber et al. |
| 8,260,010 B2 | 9/2012 | Chhibber et al. |
| 8,373,859 B2 | 2/2013 | Chhibber et al. |
| 8,527,365 B2 | 9/2013 | Pak |
| 8,564,778 B1 | 10/2013 | Igarashi |
| 8,695,610 B2 | 4/2014 | Samain et al. |
| 8,804,122 B2 | 8/2014 | Chhibber et al. |
| 8,823,934 B2 | 9/2014 | Chhibber et al. |
| 8,861,863 B2 | 10/2014 | Chhibber et al. |
| 9,171,061 B2 | 10/2015 | Minvielle |
| 9,414,623 B2 | 8/2016 | Minvielle |
| 9,429,920 B2 | 8/2016 | Minvielle |
| 9,436,170 B2 | 9/2016 | Minvielle |
| 9,460,633 B2 | 10/2016 | Minvielle |
| 9,497,990 B2 | 11/2016 | Minvielle |
| 9,528,972 B2 | 12/2016 | Minvielle |
| 9,541,536 B2 | 1/2017 | Minvielle |
| 9,564,064 B2 | 2/2017 | Minvielle |
| 9,662,061 B2 | 5/2017 | De Guia et al. |
| 9,662,062 B2 | 5/2017 | De Guia et al. |
| 9,668,653 B2 | 6/2017 | Qu |
| 9,702,858 B1 | 7/2017 | Minvielle |
| 9,805,171 B2 | 10/2017 | Baym et al. |
| 9,811,641 B2 | 11/2017 | Baym et al. |
| 2003/0014324 A1 | 1/2003 | Donovan et al. |
| 2003/0064350 A1 | 4/2003 | Rubinstenn et al. |
| 2003/0065552 A1 | 4/2003 | Rubinstenn et al. |
| 2003/0093297 A1 | 5/2003 | Schilling et al. |
| 2003/0211068 A1 | 11/2003 | O'Prey et al. |
| 2004/0081674 A1 | 4/2004 | Franke |
| 2004/0126604 A1 | 7/2004 | Wang et al. |
| 2004/0143513 A1 | 7/2004 | Aleles et al. |
| 2004/0202685 A1 | 10/2004 | Manzo |
| 2004/0236592 A1 | 11/2004 | Aleles et al. |
| 2005/0021174 A1 | 1/2005 | Wilmott et al. |
| 2005/0195316 A1 | 9/2005 | Kollias et al. |
| 2006/0092315 A1 | 5/2006 | Payonk et al. |
| 2006/0229912 A1* | 10/2006 | Negishi ............ G16H 10/20 705/2 |
| 2007/0005393 A1 | 1/2007 | Cole et al. |
| 2007/0064979 A1 | 3/2007 | Chhibber et al. |
| 2007/0064989 A1 | 3/2007 | Chhibber et al. |
| 2008/0080766 A1 | 4/2008 | Payonk et al. |
| 2009/0076639 A1 | 3/2009 | Pak |
| 2009/0083070 A1 | 3/2009 | Giftakis et al. |
| 2009/0136101 A1 | 5/2009 | Chhibber et al. |
| 2009/0141956 A1 | 6/2009 | Chhibber et al. |
| 2009/0222281 A1 | 9/2009 | Uppal |
| 2009/0245603 A1 | 10/2009 | Koruga et al. |
| 2009/0280150 A1* | 11/2009 | Kamen ............ A45D 44/002 424/401 |
| 2010/0142755 A1 | 6/2010 | Brandewie et al. |
| 2010/0245823 A1 | 9/2010 | Chhibber et al. |
| 2010/0299155 A1* | 11/2010 | Findlay ............ G16H 20/10 705/3 |
| 2010/0316296 A1 | 12/2010 | Chhibber et al. |
| 2011/0129283 A1 | 6/2011 | Samain |
| 2011/0159463 A1 | 6/2011 | Samain |
| 2011/0164263 A1 | 7/2011 | Samain et al. |
| 2011/0211047 A1 | 9/2011 | Chhibber et al. |
| 2012/0321759 A1* | 12/2012 | Marinkovich ......... A61B 5/442 356/402 |
| 2013/0309637 A1 | 11/2013 | Minvielle |
| 2014/0018634 A1* | 1/2014 | Baumann .............. G06Q 99/00 600/300 |
| 2015/0057939 A1 | 2/2015 | Baym et al. |
| 2015/0057940 A1 | 2/2015 | Baym et al. |
| 2015/0209246 A1 | 7/2015 | Haslacher |
| 2017/0262598 A1* | 9/2017 | Petkov .................. G06T 15/06 |
| 2017/0270593 A1* | 9/2017 | Sherman ................ G06N 3/082 |
| 2017/0281526 A1 | 10/2017 | Dersh et al. |
| 2018/0014777 A1* | 1/2018 | Amir .................... A61B 5/444 |

FOREIGN PATENT DOCUMENTS

| | | |
|---|---|---|
| WO | 2012159012 A1 | 11/2012 |
| WO | 2015116875 A1 | 8/2015 |
| WO | 2017173291 A1 | 10/2017 |

OTHER PUBLICATIONS

Lavender, Tina, "Randomized, Controlled Trial Evaluating a Baby Wash Product on Skin Barrier Function in Healthy, Term Neonates," JOGNN, 42, 203-214; 2013. DOI 10.1111/1552-6909.12015 (Year: 2013).*

International Application No. PCT/US2019/015448 Annex to Form PCT/ISA/206 Partial International Search dated Apr. 12, 2019 (14 pages).

* cited by examiner

SKIN HISTORY + ROUTINE

Tell us what matters most to you about your skin and what products you are currently using. This will help us make sure your Atolla is tailored to fit into your existing routine!

Skin goals  SELECT ALL THAT APPLY
- ☒ Learning more about my skin
- ☐ Tracking my skin progress
- ☐ Achieving my skin goals
- ☐ A personalized formula

Skin concerns  SELECT ALL THAT APPLY
- ☐ Acne
- ☐ Congestion / Blackheads
- ☐ Discoloration / Spots
- ☒ Dryness
- ☐ Redness / Irritation
- ☐ Sun Damage
- ☐ Wrinkles / Fine Lines

What is your most important skin concern?
Dryness

What is your second-most important skin concern?
Redness / Irritation

Current products

| Atolla Personalized Serum (pm) | ■ Use daily | ☐ Use weekly |
| Cetaphil Gentle Skin Cleanser (am, pm) | ■ Use daily | ☐ Use weekly |
| Drunk Elephant T.L.C. (pm) | ☐ Use daily | ■ Use weekly |
| Embryolisse Lait-Creme (am) | ■ Use daily | ☐ Use weekly |
| Sunscreen | ☐ Use daily | ☐ Use weekly |
| Toner | ☐ Use daily | ☐ Use weekly |
| Kiehl's Deep Pore Cleansing Masque (pm) | ☐ Use daily | ■ Use weekly |

What's your favorite skincare product you've used recently?
Embryolisse Lait-Creme Any skincare product you've used that you haven't liked?
Neutrogena Rapid Clear Scrub

Is your skin sensitive?
- ● Yes
- ○ No
- ○ I don't know

How sensitive is your skin to the sun?
- ○ I always burn (do not tan)
- ○ I burn easily (tan poorly)
- ● I tan after initial burn
- ○ I burn minimally (tan easily)
- ○ I rarely burn (tan darkly easily)
- ○ I never burn (always tan darkly)

How happy are you with your skin?

BACK  CONTINUE

1000

YOUR PERSONALIZED PRODUCT

Carrier

* Jojoba

Active

* Calendula
* Echium

FORMULATION BREAKDOWN

* Jojoba

NON-GREASY EMOLLIENT; ODORLESS; RESTORATIVE; MOISTURE-RETAINING due to Vitamin E and B || #dryness #redness #wrinkles

* Calendula

HEALING, ANTIBACTERIAL, CAROTENOIDS, ANTI-AGING, ANTI-INFLAMMATORY || #acne #dryness #redness || +3

* Echium

ANTI-INFLAMMATORY, SOOTHING, GLA (gamma-linolenic acid), HIGH IN PUFAS (Omega 3+6) || #dryness #wrinkles || +3

FIG. 10

SYSTEMS AND METHODS FOR FORMULATING PERSONALIZED SKINCARE PRODUCTS

RELATED APPLICATION

This application is a continuation of U.S. patent application Ser. No. 16/259,831, filed Jan. 28, 2019, which claims the benefit of U.S. Provisional Patent Application No. 62/623,207, filed on Jan. 29, 2018 and entitled "Systems and Methods for Formulating Personalized Skincare Products." The entire contents of both of these applications are hereby incorporated by reference in their entirety.

TECHNICAL FIELD

This application relates generally to systems, methods and apparatuses, including computer programs and algorithms, for formulating skincare products. More specifically, this application relates to systems and methods for formulating personalized skincare products and recommending personalized skincare product routines based on user-specific data.

BACKGROUND

Many or most skincare products today are targeted at large swaths of consumers, but several problems arise when formulating skincare products for a mass market. One problem is how to accommodate the largest possible number of diverse skin types for any given product claim made. This may explain the proliferation of skin "type" products in the market (which may include, for example, oily, dry, combination, acne prone, sun sensitive, sensitive, allergy tested, poor texture, or large pores). When targeting a mass market, manufacturers must strike a balance between what is economically feasible for them relative to the quantity of products available in the market and the number of customers they can attract from the market.

Several companies today are creating "customized" products for customers. The methods employed by these companies generally fall into two groups: (1) using self-reported answers about skin concerns to recommend an existing product, or (2) using self-reported answers about skin concerns to design customized skin care formulations. One problem with both approaches is that that self-reported data can be unreliable, e.g., because customers have little objective knowledge of their skin. The first approach also suffers from the restriction of a limited set of potential products, all of which have typically been created for the mass market. The second approach has suffered from limited effectiveness of results.

SUMMARY

Accordingly, the invention provides a novel framework, including a computing system and associated computing methods, algorithms and modules, for (1) determining skin health and/or issues at one or more points in time, and (2) providing unique skin care product recommendations, formulation parameter recommendations, and/or product routines to individual users on a customized, ongoing (e.g., iterative) basis. Thus, the invention enables personal skincare product and regimen creation, recommendation, and refinement over time.

In some embodiments, the invention can be implemented on one or more computerized systems located at a retail location (e.g., conducted by a sales associate or self-guided by the consumer without assistance), a spa or office (e.g., conducted by an esthetician, skin specialist, or dermatologist, or self-guided by the customer without assistance), or at home (e.g., conducted by a consumer without further assistance). In some embodiments, the invention includes collecting data specific to an individual user, e.g., objective dermal data, visual skin data, demographic data, environmental data, genetic data, diet data, preference data, and other data. In some embodiments, a computer-implemented machine learning algorithm uses the data provided to specify unique skincare product formulations, existing products, and specific ingredient recommendations. In some embodiments, the invention recommends lifestyle, diet, and/or holistic wellness tips to achieve desired skin results.

After using recommended existing product(s), personalized skincare product(s) or implementing a lifestyle or diet change, the user can provide feedback on the efficacy of the product(s) and update his or her skin data points outlined above. Next, the product formulation(s) can be refined based on recommendations generated by the algorithm(s). These reformulations can occur due to, for example, seasonal changes, locational or environmental changes, observed changes in the user's skin, and anticipated changes in the user's skin. In some embodiments, the feedback cycle of recommendation, use, feedback, and revision aids the success of this invention. In some embodiments, the invention uses prior feedback and/or aggregate skin data and patterns to make new or revised recommendations.

The invention overcomes prior limitations in formulating skin products for the mass market by providing a customized product designed based on an individual's unique skin data. Thus, the customized product is created to address an individual's unique skin concerns and/or suit the individual's preferences, and can be changed based on environment, lifestyle, and how the individual's skin changes over time. In some embodiments, aggregate skin data from multiple users allows predictive analytics and machine learning to be used to recommend ingredients that are found to be the safest and most efficacious for the user based on his or her individual skin, and refine the recommendations based on individual response and preferences. In some embodiments, the feedback received from the user is fed back into one or more algorithms to further refine the recommendations and recommend more accurate and effective ingredients tailored to each user.

In some embodiments, the present invention uses data specific to a user (e.g., dermal data, visual skin data, demographic data, environmental data, genetic data, diet data, preference data, and other data) in systems and methods (e.g., one process for an in-person setting and another for a home setting) that leverages one or more computerized (e.g., machine learning or deep learning) algorithms to make unique, personal skin care products, other wellness products, and personalized recommendations on an ongoing basis. In some embodiments, creating a feedback loop of recommendation, use, outcome, and revision helps to ensure that each product provides a benefit to the user and that the skincare products, wellness products, and personalized recommendations for each user evolve as his or her concerns, environment and skin change over time.

An example of possible, but not limiting, data gathering techniques and associated skin property is listed in the following table:

| Technique | Skin Property |
|---|---|
| Trans-epidermal water loss | Barrier function |
| Corneometry | Skin Moisture |
| Chromametry | Skin Color |
| Cutometry | Skin Elasticity & Firmness |
| Sebumetry | Skin sebum |
| Sonography | Skin thickness |
| Profilometry | Skin roughness |
| Laser-Doppler flowmetry | Blood flow |
| Visible Imaging | Wrinkles, texture, dark circles, spots, pore size |
| Ultra-Violet Imaging | Photo-damage, oil balance, bacteria |
| Skin pH | Relative acid-alkaline property of skin |

In one aspect, the invention features a computerized method of formulating a skincare product for a user. The method includes receiving, by a computing device, data inputs including one or more hydration level measurements of the user's skin, one or more oil level measurements of the user's skin, and a photograph of the user's skin reflecting a set of skin concerns. The method also includes determining, by the computing device, based on the one or more hydration level measurements, a normalized hydration index score. The method also includes determining, by the computing device, based on the one or more oil level measurements, a normalized oil index score. The method also includes determining, by the computing device, based on the photograph of the user's skin, a set of normalized severity scores corresponding to a set of skin concerns of the user. The method also includes generating, by the computing device, a first skin health data set including the normalized hydration index score, the normalized oil index score, and the set of normalized severity scores. The method also includes storing, by the computing device, the first skin health data set in first memory in electronic communication with the computing device. The method also includes determining, by the computing device, based on the first skin health data set, a first skin health metric. The method also includes storing, by the computing device, the first skin health metric in second memory in electronic communication with the computing device. The method also includes determining, by the computing device, using a machine learning framework operating on the computing device, one or more first skincare product formulations based on the first skin health metric and the first skin health data set. The method also includes storing, by the computing device, the one or more first skincare product formulations in third memory in electronic communication with the computing device.

In some embodiments, the method includes receiving, by the computing device, one or more additional data inputs reflecting changes in at least one of hydration level measurements, oil level measurements or skin concerns after use of the one or more first skincare product formulations by the user; and/or generating, by the computing device, based on the one or more additional data inputs, a second skin health data set, by (i) calculating, by the computing device, percentage changes in hydration level measurements, oil level measurements, and the normalized severity scores (or a pre-cursor to this data, e.g., raw data or pre-processed data such as a black-to-white ratio described in further detail below); and (ii) calculating, by the computing device, the second skin health data set based on the first skin health data set and the percentage changes; and/or determining, by the computing device, using the machine learning framework operating on the computing device, one or more second skincare product formulations based on the second skin health data set.

In some embodiments, the data inputs further include at least one of user age, sex, ethnicity or occupation. In some embodiments, the photograph is taken with at least one of visible light or ultraviolet light. In some embodiments, the one or more data inputs include information reflecting at least one of temperature, humidity, or environmental ultraviolet index of the user's location. In some embodiments, the one or more data inputs include information reflecting at least one of user genetics, medical history, diet, water intake, smoking habits, known allergies, alcohol habits, sleep quality, stress levels, time spent in front of electronic screens, or sun exposure. In some embodiments, the one or more data inputs include information reflecting at least one of a user-reported assessment of skin health, skincare product usage, past skincare product usage, past skin reactions, skincare goals, skincare concerns, skincare, absorption or texture preferences. In some embodiments, the one or more data inputs include at least one of an elasticity measurement of the user's skin, a wrinkle measurement of the user's skin, or a surface pH level of the user's skin. In some embodiments, the first skin health data set includes information reflecting at least one of the user's wrinkles, dark spots, dark circles, texture, acne, sun damage, pore size, redness, or other skin damage. In some embodiments, the first skincare product formulation includes information reflecting active ingredients, preservatives, dosage, and/or a unique user skin identifier.

In some embodiments, the method further includes generating, by the computing device, based on the first skin health data set, first formulation instructions for manufacturing a first skincare product by a formulation specialist or machine. In some embodiments, the method further includes generating, by the computing device, based on the first skin health data set, one or more recommendations for adjustments to the user's lifestyle, diet, or holistic wellness to achieve a desired skin result. In some embodiments, the method further includes generating, by the computing device, based on the first skin health data set, a personalized skin care routine including a recommendation for at least one of a cleanser, a serum, a facial oil, a moisturizer, dietary supplements, or a sunscreen. In some embodiments, the method further includes (i) generating, by the computing device, a user display data set for interpretation and display by a user computing device in electronic communication with the computing device, and/or (ii) sending the user display data set to the user computing device. In some embodiments, the method further includes receiving, by the computing device, user certification of the first skincare product formulation prior to storing the first skincare product formulation in memory.

In another aspect, the invention features a method of manufacturing a skincare product for a user. The method includes receiving, by a manufacturing system, a product formulation having a unique skin identifier for the user and based on a unique skin health data set of the user. In some embodiments, the product formulation includes at least one ingredient. The method also includes compounding, by the manufacturing system, a customized skincare product according to the product formulation. The method also includes bottling, by the manufacturing system, the customized skincare product in a container. The method also includes labeling, by the manufacturing system, the container with a label displaying the at least one ingredient.

In another aspect, the invention features a computing system for formulating a skincare product for a user. The system includes a computing device configured to perform the following functions: (i) receive data inputs including one or more hydration level measurements of the user's skin, one or more oil level measurements of the user's skin, and a photograph of the user's skin reflecting a set of skin concerns; (ii) determine, based on the one or more hydration level measurements, a normalized hydration index score; (iii) determine, based on the one or more oil level measurements, a normalized oil index score; (iv) determine, based on the photograph of the user's skin, a set of normalized severity scores corresponding to a set of skin concerns of the user; (v) generate a first skin health data set including the normalized hydration index score, the normalized oil index score, and the set of normalized severity scores; (vi) store the first skin health data set in first memory in electronic communication with the computing device; (vii) determine, based on the first skin health data set, a first skin health metric; (viii) store the first skin health metric in second memory in electronic communication with the computing device; (ix) determine, using a machine learning framework operating on the computing device, one or more first skin care product formulations based on the first skin health metric and the first skin health data set; and (x) store, the one or more first skincare product formulations in third memory in electronic communication with the computing device. In some embodiments, the system includes a user computing device in electronic communication with the computing device, the user computing device for collecting and providing the data inputs to the computing device. In some embodiments, the first storage and the second storage are included in a database in electronic communication with the computing device.

In another aspect, the invention features a computerized method of formulating first and second skincare products for a user. The method includes receiving, by a computing device, one or more first data inputs reflecting dermal information of the user. The method also includes generating, by the computing device, based on the one or more first data inputs, a first skin health data set for the user, the first skin health data set including one or more normalized scores reflecting the one or more first data inputs. The method also includes storing, by the computing device, the first skin health data set in first storage in electronic communication with the computing device. The method also includes determining, by the computing device, a first skincare product formulation based on the first skin health data set. The method also includes storing, by the computing device, the first skincare product formulation in second storage in electronic communication with the computing device. The method also includes receiving, by the computing device, one or more second data inputs reflecting changes in the first data inputs after use of a first skin care product based on the first skin care product formulation. The method also includes generating, by the computing device, based on the one or more first data inputs and one or more second data inputs, a second skin health data set for the user. The method also includes storing, by the computing device, the second skin health data set in third storage in electronic communication with the computing device. The method also includes determining, by the computing device, a second skincare product formulation based on the second skin health data set. The method also includes storing, by the computing device, the second skincare product formulation in fourth storage in electronic communication with the computing device.

In another aspect, the invention features a computerized method of training a machine learning framework to generate one or more skincare product formulations. The method includes receiving, by a computing device, for multiple users, first data inputs including one or more hydration level measurements of each user's skin, one or more oil level measurements of each user's skin, and a photograph of each user's skin reflecting a set of skin concerns. The method also includes determining, by the computing device, for each user, a corresponding first skin health data set and a corresponding first skin health metric based on the first data inputs. The method also includes determining, by the computing device, for each user, one or more recommended first skincare product formulations based on the first skin health metric and/or the first skin health data set. The method also includes receiving, by the computing device, one or more second data inputs reflecting changes in the first data inputs after use of a first skin care product based on the first skin care product formulation. The method also includes combining, by the computing device, the one or more second data inputs with the first data inputs and the first skin health data set to create a training data set. The method also includes calculating, by the computing device, a second skin health metric based on the one or more second data inputs. The method also includes determining, by the computing device, using the second health data set and a machine learning framework, a machine learning model. The method also includes determining, by the computing device, for each user, one or more associations between the data inputs for the user and the one or more first skincare product formulations for the user, each association based on the corresponding first skin health data set and the corresponding first skin health metric for each user. The method also includes storing, by the computing device, the model in memory in electronic communication with the computing device. In some embodiments, other data inputs can be measured, inputted, transformed via algorithms, calculated and/or manipulated as described above with respect to other aspects of the invention.

BRIEF DESCRIPTION OF THE DRAWINGS

The advantages of the invention described above, together with further advantages, may be better understood by referring to the following description taken in conjunction with the accompanying drawings. The drawings are not necessarily to scale; emphasis is instead generally placed upon illustrating the principles of the invention.

FIGS. 9A-9C are screen shots of a user questionnaire eliciting certain dermal data, according to an illustrative embodiment of the invention.

FIG. 10 is a screen shot of a skin care product recommendation, according to an illustrative embodiment of the invention.

DETAILED DESCRIPTION

Figure 1:
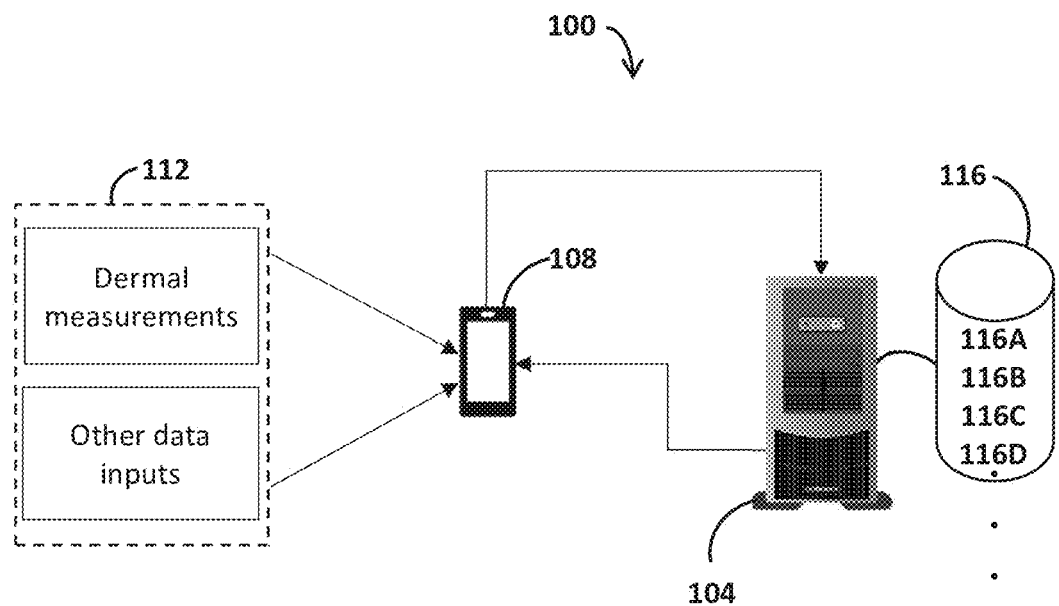
FIG. 1 is a schematic diagram of a computing system for formulating a skin care product for a user, according to an illustrative embodiment of the invention.

FIG. 1 is a schematic diagram of a computing system 100 for formulating a skin care product for a user, according to an illustrative embodiment of the invention. The computing system 100 includes a server computing device 104 (or a different back-end computing device) and a user computing device 108 (e.g., a mobile phone, tablet, or different front-end computing device) in electronic communication with the server computing device 104 (e.g., via the Internet). During operation, the user computing device 108 captures data inputs 112 reflecting dermal information (e.g., information relevant to skin properties usable by the system 100) of the user, e.g., via an application installed on the user computing device 108. In some embodiments, the data inputs 112 include one or more dermal measurements (e.g., one or more hydration level measurements of the user's skin and/or one or more oil level measurements of the user's skin) and one or more other data inputs (e.g., one or more photographs of the user's skin, taken with visible and/or ultraviolet light, using either the user's smartphone camera or another photographic device) reflecting a set of skin concerns (e.g., wrinkles, dark spots, dark circles, acne, sun damage, redness, or other skin damage). In some embodiments, the data inputs 112 include other variables, such as at least one of a user age, sex, ethnicity, or occupation. In some embodiments, the data inputs 112 include information reflecting at least one of temperature, humidity, or environmental ultraviolet index of the user's location. In some embodiments, the data inputs 112 include information reflecting at least one of the additional variables shown and described in greater detail below in FIG. 6. In some embodiments, some of the data inputs 112 are captured via a user interface such as the one shown and described below in FIG. 9.

After the data inputs 112 are captured, they are sent to the server computing device 104 via an electronic communication (e.g., over an electronic transmission medium). The server computing device 104 receives the data inputs 112 and determines (e.g., computes), based on the data inputs 112, one or more transformed skin health variables, e.g., a normalized hydration score, a normalized oil index score, and/or a normalized set of severity scores for a set of skin concerns for the user's skin. The specific algorithms used may be as shown in greater detail below in FIGS. 3-5. The server computing device 104 then generates a first skin health data set including the calculated scores (and potentially other information, e.g., of the type shown below in FIG. 6), and stores them in first memory 116A in electronic communication with the server computing device 104. The server computing device 104 then determines, using a machine learning (e.g., a deep learning) framework operating on the server computing device 104, one or more first skin care product formulations (and/or skin care routines) based on the first skin health data set. In some embodiments the machine learning framework includes an ensemble of GRU or LSTM recurrent neural network and optimization algorithms. The server computing device 104 then stores the one or more first skin care product formulations (and/or skin care routines) in second memory 116B in electronic communication with the server computing device 104.

After performing the above calculations, the server computing device 104 sends the calculated first skin health data set, recommended skin care product formulations, and/or recommended skin care routines to the user computing device 108 for display to the user in the form of a recommendation. The recommendation includes one or more personalized skin care products in a specific routine for the user to utilize, e.g., on a temporary or a permanent basis. The products can have ingredients and other aspects specific to the user and optimized to help the user achieve his or her maximum skin health. In some embodiments, the recommendation is displayed for the user via a user interface of the user computing device 108, e.g., in the form shown and described below in greater detail in FIG. 10.

After the user has adopted the recommendation for a period of time, it is expected that one or more aspects of the prior data inputs 112 may change in response to the user's adopting the recommendation. The computing system 100 can receive updated data inputs reflecting changes in the prior data inputs and generate further skin health data sets over time, and thus iteratively better define an optimal skin care recommendation for the user. In some embodiments, the server computing device 104 can receive one or more additional data inputs reflecting changes in at least one of hydration level measurements, oil level measurements or skin photography reflecting skin concerns after use of the one or more first skin care product formulations by the user. In some embodiments, the server computing device 104 can generate, based on the one or more additional data inputs, a second skin health data set, e.g., by (i) calculating, by the computing device, percentage changes in the hydration level measurements, the oil level measurements, and the normalized severity scores; and (ii) calculating, by the computing device, the second skin health data set based on the first skin health data set and the percentage changes. In some embodiments, the server computing device 104 can determine, using the machine learning framework operating on the server computing device 104, one or more second skin care product formulations based on the second skin health data set. Additional memory (e.g., third memory, fourth memory, and so on, corresponding to elements 116C, 116D, and so on) can be made available and in electronic communication with the server computing device 104 for storing further information generated and/or received by the server computing device 104. The memory components 116A, 116B, 116C, 116D, etc., can be stored in a single database 116 in electronic communication with the server computing device 104.

Figure 2:
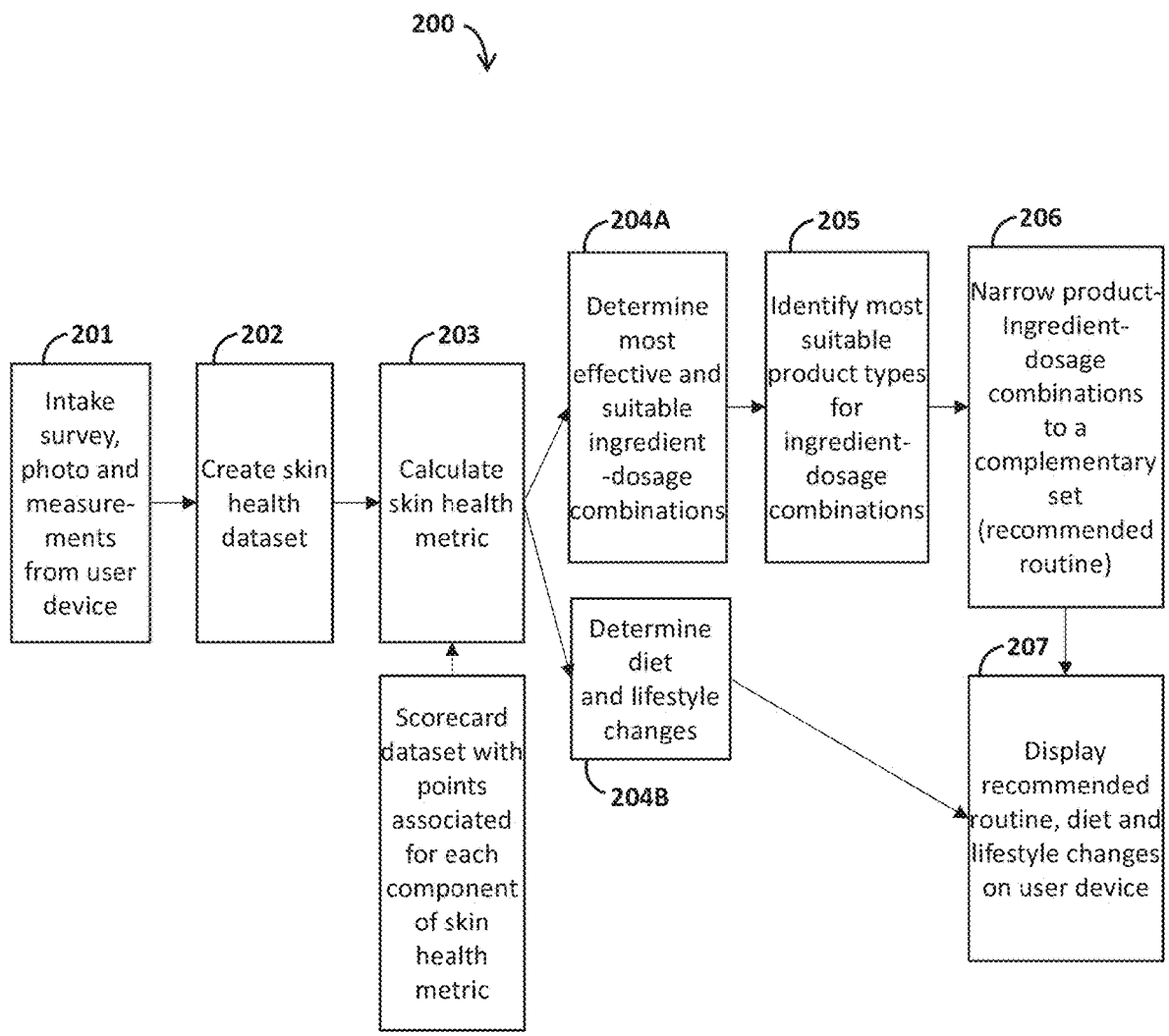
FIG. 2 is a flow diagram illustrating a method of formulating a skin care product for a user, according to an illustrative embodiment of the invention.

FIG. 2 is a flow diagram 200 illustrating a more detailed method of formulating a skin care product for a user, according to an illustrative embodiment of the invention. These method steps can be implemented using the computing system 100 shown and described above in FIG. 1. In a first step 201, a user provides to a mobile device application a set of answers to intake survey questions, one or more photos of the user's skin, and one or more measurements provided via the user device. In a second step 202, the computing device creates a skin health data set, e.g., as described above. In a third step 203, the computing device calculates a skin health metric. The skin health metric can be based on a scorecard data set with points associated with each component of the skin health metric. For example, consider a case in which four data points in the scorecard are smoking habits, severity scores, hydration index and oil index. For example, if a person does not ever smoke, that may equate to 100 points; if the person does smoke very frequently, that may equate to 0 points. Similarly, the severity scores, hydration index and oil index are translated to a scale of 0-100, with 0 representing most unhealthy and 100 representing most healthy. Thus, for a person who does not ever smoke, has one skin issue (e.g., discoloration) with a severity score of 50, and hydration and oil indices of 60 each, his or her skin health metric would equal 270. In a fourth step 204, the computing device determines one or more ingredient-dosage combinations (see 204A) that will be effective and suitable (e.g., the most effective and suitable) to improve the user's skin health given the user's input data, and/or determines diet and lifestyle changes that will be effective to improve the user's skin health given the user's input data (see 204B). In a fifth step 205, the computing device identifies product types that correspond to the previously determined ingredient-dosage combinations. In a sixth step 206, the computing device narrows the product-ingredient-dosage combinations to a complementary set, e.g., a recommended routine. In a seventh step 207, the computing device displays the recommendations for the user, e.g., routine, diet, and lifestyle changes.

Figure 3:
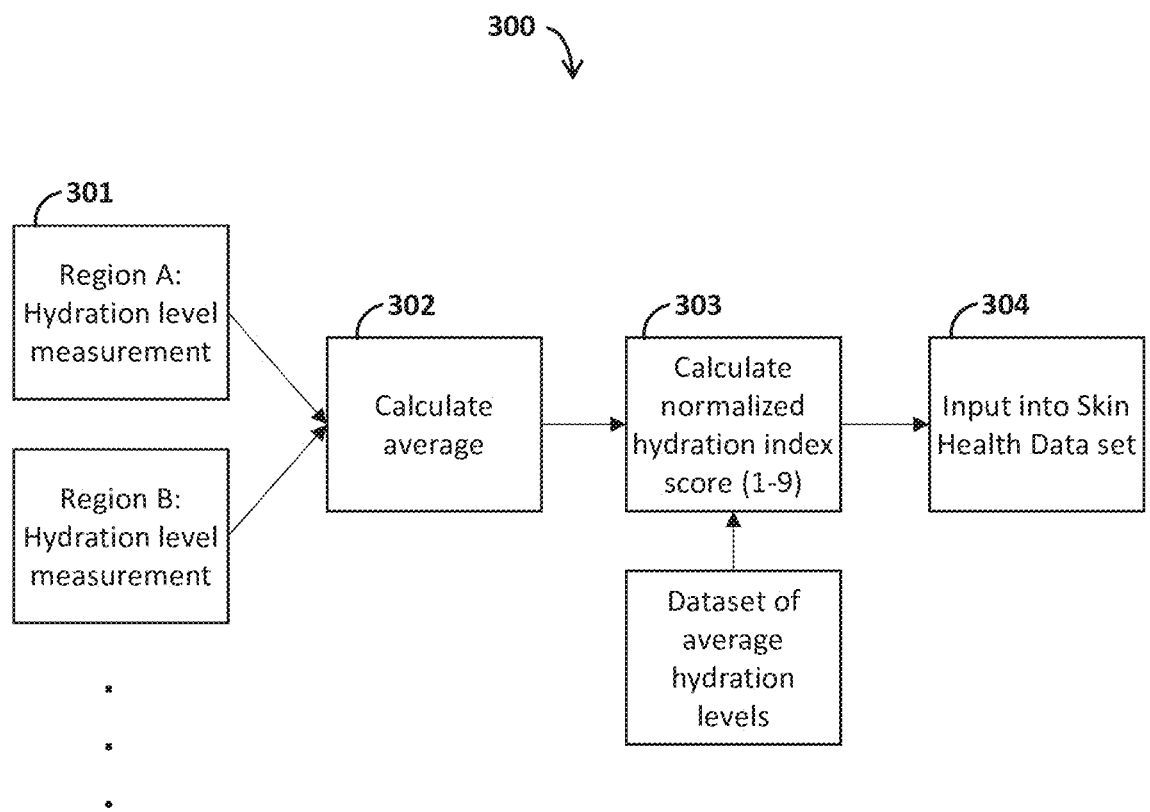
FIG. 3 is a flow diagram illustrating a computerized method of calculating a normalized hydration index score for a user's skin, according to an illustrative embodiment of the invention.

FIG. 3 is a flow diagram 300 illustrating a computerized method of calculating a normalized hydration index score for a user's skin, according to an illustrative embodiment of the invention. The method can be implemented on a computing device, e.g., the server computing device 104 shown and described above in FIG. 1. In a first step 301, hydration measurements are taken at one or more locations on the user's skin (e.g., in regions A, B, etc. as shown). The measurements can be collected by conducting a corneocyte test, which measures skin "desquamation" or shedding of the outer layers of the skin using a medical adhesive. The user can take a picture of the completed test on the medical adhesive. A computer vision algorithm trained on a dataset of corneocyte test results can estimate the hydration level measurement level (e.g., a percentage hydration) of the skin. Each hydration level measurement can be transformed into a hydration measurement number. In some embodiments, a bioimpedence electrical analysis tool can also be used to gather input measurements. In a second step 302, the hydration measurement numbers are averaged. The hydration measurement numbers from several parts of the user's face and body can be weighted based on a relative importance dataset (e.g. the face may have a higher weight than the neck for a facial product formulation). In a third step 303, the average is compared with a data set of average hydration levels collected for a set of reference users (e.g., for a comparable region or skin location), and a normalized hydration index score (e.g., 1-9 or another appropriate numerical scale) is generated. In a fourth step 304, that normalized hydration index score is used as an input into, and/or recorded a component of, a skin health data set for the user (e.g., a first skin health data set).

Figure 4:
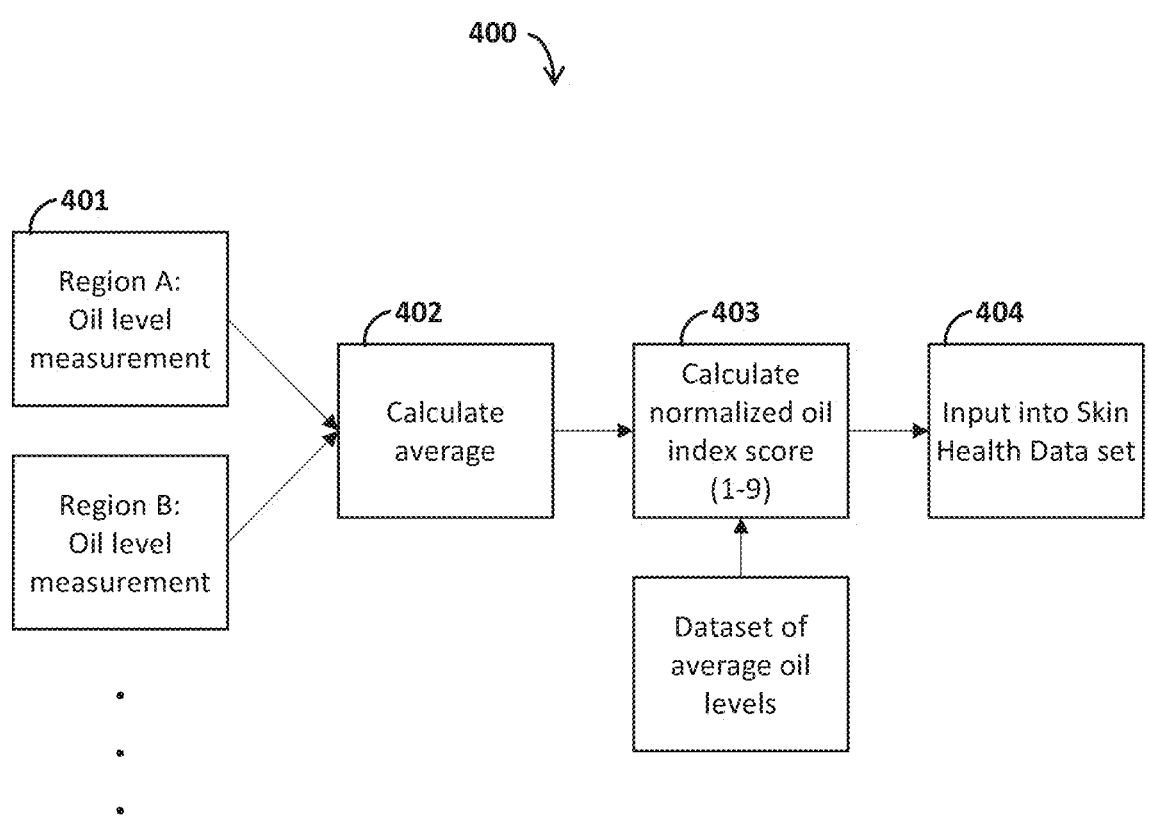
FIG. 4 is a flow diagram illustrating a computerized method of calculating a normalized oil index score for a user's skin, according to an illustrative embodiment of the invention.

FIG. 4 is a flow diagram 400 illustrating a computerized method of calculating a normalized oil index score for a user's skin, according to an illustrative embodiment of the invention. The method can be implemented on a computing device, e.g., the server computing device 104 shown and described above in FIG. 1. In a first step 401, oil measurements are taken at one or more locations on the user's skin (e.g., in regions A, B, etc., possibly corresponding to the same regions A, B, etc. shown and described above). The measurements can be collected by conducting a sebum test. The sebum test can use an oil absorbing film over a black background—e.g., oil or sebum from the skin makes the film on the top layer transparent upon contact, so a black gradient appears (the darker the gradient pattern, the oilier the skin). The user takes a picture of the completed test. A computer vision algorithm trained on a dataset of sebum test results estimates the raw oil measurement level (e.g., a percentage oil) of the skin. Each oil level measurement can be transformed into an oil measurement number. In some embodiments, a photometric sensor and/or a bioimpedence electrical analysis tool can also be used to collect input measurements. In a second step 402, the oil measurement numbers are averaged. The raw oil measurements from multiple parts of the user's face and body can be weighted based on a relative importance dataset (e.g., a face can be weighted higher than a neck, as in the application described above). In a third step 403, the average is compared with a data set of average oil levels collected for a set of reference users (e.g., for a comparable region or skin location), and a normalized oil index score (e.g., 1-9 or another appropriate numerical scale) is generated. In a fourth step 404, that normalized oil index score is used as an input into, and/or recorded a component of, the skin health data set for the user.

Figure 5:
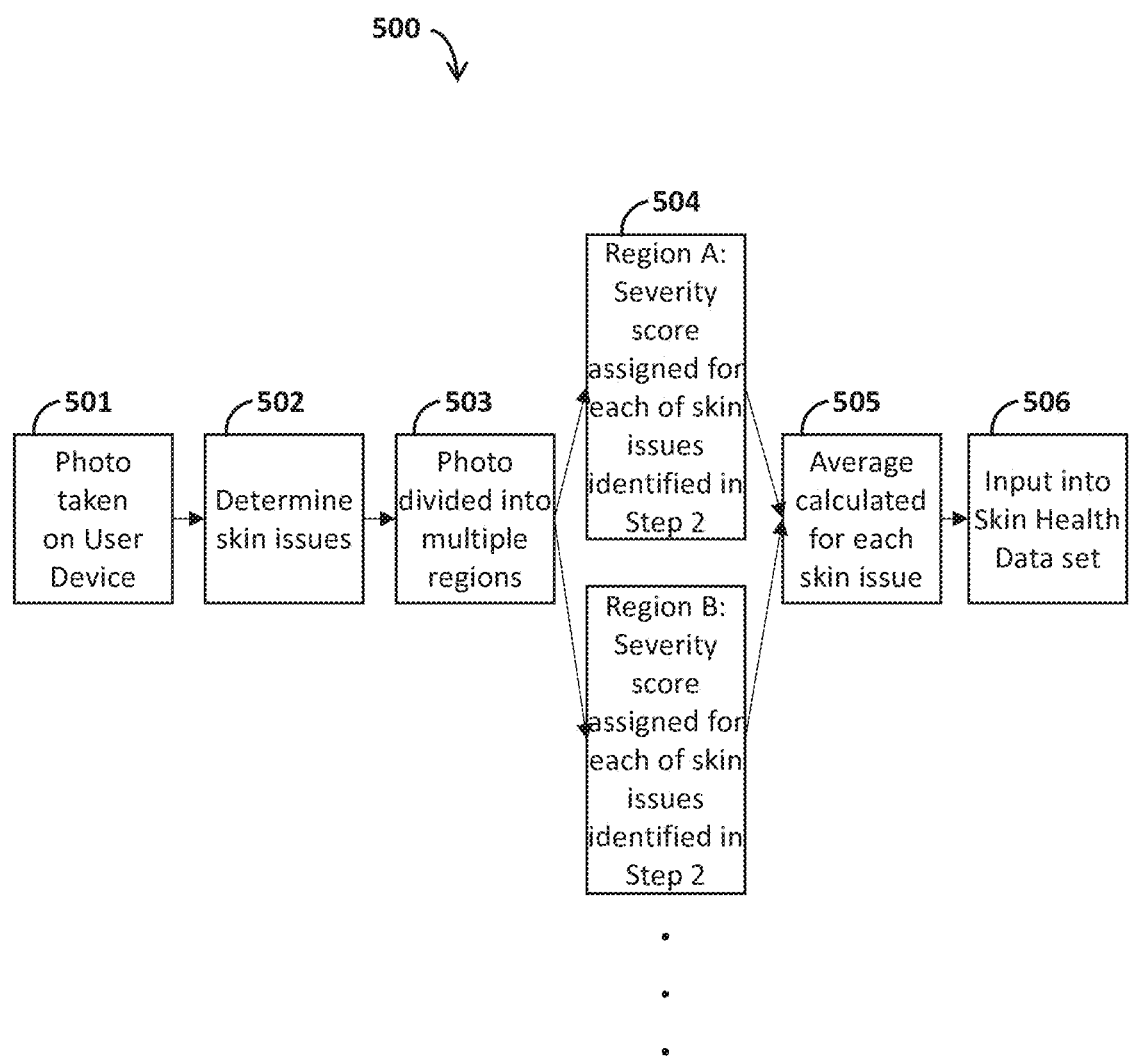
FIG. 5 is a flow diagram illustrating a computerized method of calculating a normalized set of severity scores for a user's skin, according to an illustrative embodiment of the invention.

FIG. 5 is a flow diagram 500 illustrating a computerized method of calculating a normalized set of severity scores for a user's skin, according to an illustrative embodiment of the invention. This method can be implemented using a computer vision diagram implemented on a computing device (e.g., the server computing device 104 shown and described above in FIG. 1). In a first step 501, a photograph of the user's skin is taken, e.g., on a user computing device or in a physical store location. In a second step 502, the computer vision engine determines any skin issues of the user. In one embodiment, the computer vision engine first makes illumination adjustments based on a quadratic model of global illumination. Second, multiple copies of the illumination-adjusted photograph are created, e.g., one for each skin issue. Different computer algorithms can be used to assess each skin issue. For example, to assess if a user has wrinkles, one of the image copies can be transformed using Gabor or Hessian filters and/or image morphology. The algorithm can calculate the ratio of white to black in the image after converting to grayscale. If the ratio is above a preset threshold, the algorithm determines that the user has wrinkles.

In a third step 503, the photograph is divided into multiple regions, e.g., Region A, Region B, etc. Specific regions of the skin can be chosen to measure the severity of the skin issue (e.g. left cheek, right cheek, forehead, under-eye, etc.). A region map can be overlaid on top of the photograph. Using the transformed copies of the photograph, an algorithm can use the region map to divide each transformed image copy into regions. In a fourth step 504, a severity score can be assigned for each region identified in step 503 for each skin issue identified in step 502 (e.g., for a skin photograph having N skin issues divided into M regions, the severity scores may occupy an N×M matrix). Different computer algorithms can be used for each skin issue to assess the severity. For example, for a user with discoloration, the image can be transformed into a HSV color space. Using line-fitting threshold method, the pigmentation appears as white in grayscale. The algorithm calculates the ratio of white to black. The ratio is normalized to index after comparing with dataset of other users. In a fifth step 505, an average severity score is calculated for each skin issue, e.g., a vector of dimension N is generated representing the set of average severity scores for each of N skin issues identified. In a sixth step 506, that vector is used as an input into, and/or recorded a component of, the skin health data set for the user.

In some embodiments, the computer vision algorithm makes illumination adjustments based on a quadratic model of global illumination. A computer vision algorithm analyzes a region of the user's skin (e.g., face) to determine if the user has a skin issue (e.g., a binary determination of "yes" or "no") such as wrinkles, clogged pores, breakouts, redness, or discoloration. The computer vision algorithm can be based on a trained machine learning model, e.g., an anomaly detection model or a convolutional neural network. A different computer algorithm can be used for each skin issue to assess the severity of the issue. As an example, to assess a user's wrinkles, one region of a skin image can be transformed using a Gabor or a Hessian filter with image morphology. The algorithm can then calculate gradient of white-to-black after converting to grayscale. The gradient score can then be normalized to an index after comparing with a data set of other users. As another example, to assess a user's skin discoloration, one region of a skin image can be transformed into an HSV color space. Pigmentation in grayscale can be extracted using a line-fitting threshold method. An algorithm calculates a gradient of white-to-black after converting to grayscale. A gradient score is normalized to an index after comparing it with data set of other users.

Figure 6:
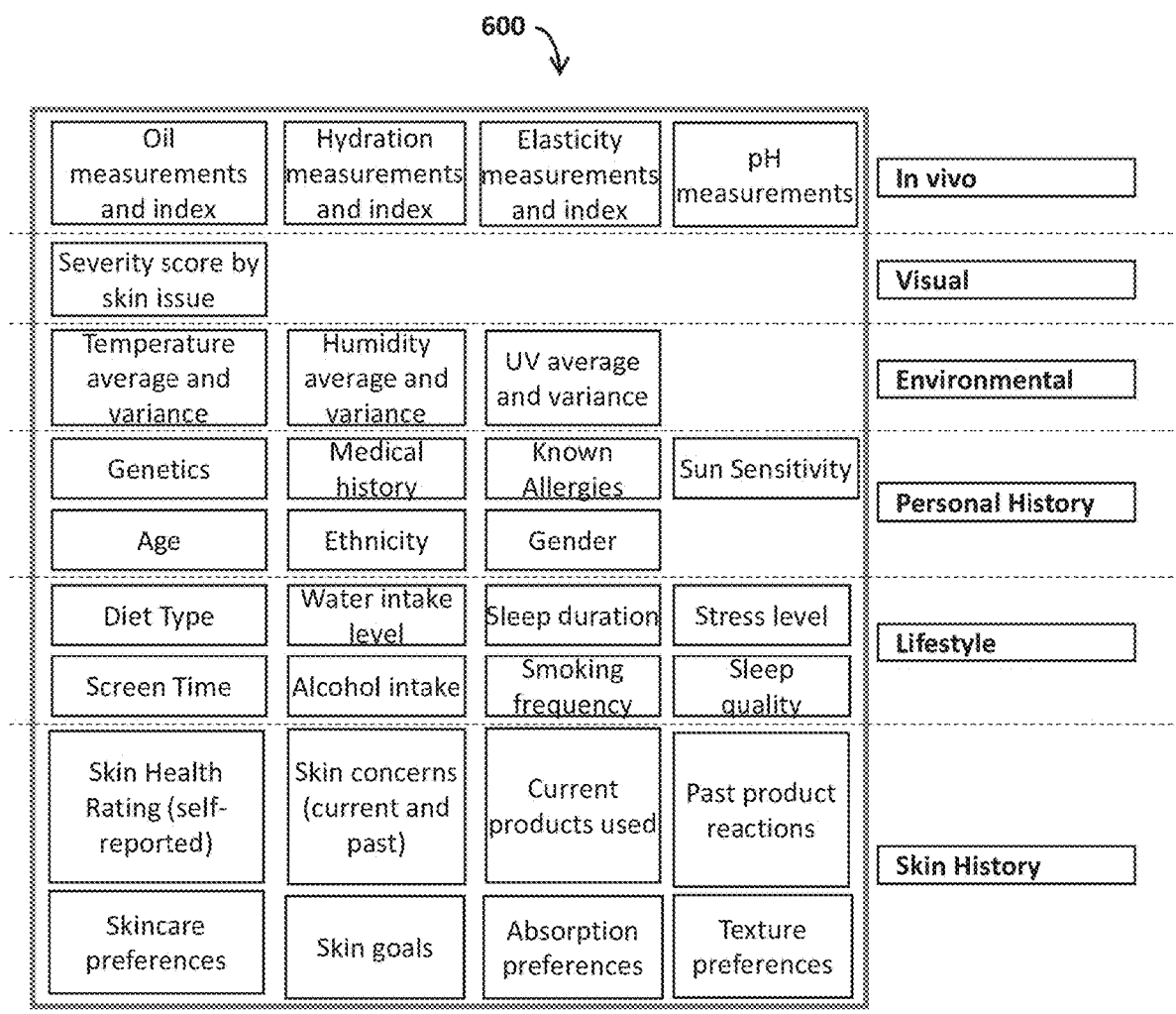
FIG. 6 is a schematic diagram illustrating exemplary components of a skin health data set, according to an illustrative embodiment of the invention.

FIG. 6 is a schematic diagram 600 illustrating exemplary components of a skin health data set, according to an illustrative embodiment of the invention. The skin health data set can include one or more of the components included in FIG. 6. One having ordinary skill in the art will readily appreciate that associations between skin health and/or skin product recommendations can be drawn using other variables as well, and would regard the exemplary data set shown in FIG. 6 as significant but not exhaustive of all possible skin variables. In some embodiments, the skin health data set includes variables that can be sub-categorized into groupings of (i) in vivo, (ii) visual, (ii) environmental, (iv) personal history, (v) lifestyle, and (vi) skin history. Each of the variables can be stored in a single database or in separate memory, e.g., in an Excel spreadsheet, in a plain text file, or in HTML form. Each of these variables can represent or provide the basis for an input (e.g., 112 as shown and described above in FIG. 1).

In one example relating to weather and UV, a computer program inputs a user's zip code into a public online weather database and stores in a temporary data set the temperature (Fahrenheit) values, humidity values (percentage) and UV Index for each of the last thirty days. A computer algorithm calculates the average and variance of each of these variables. The average and variance for each of these data inputs calculated by the computer algorithm are stored in the first skin health data set. For several of the personal history (e.g., genetics) and/or lifestyle (e.g., genetics) data inputs, a computer algorithm can compare the data input value against a data table with pre-determined buckets for the variable. The bucket value and the raw data input can in turn be stored in the first skin health dataset. For several of the skin history data inputs (e.g., products used), user input can be matched to an official database (e.g., current skincare products used can be matched, either by manual or by bar code, to an official product name by searching through a skincare product database. In an example involving user preferences, based on responses to preference indicator questions or sample ingredient trials, the user can be assigned to a preference profile. In one embodiment, a computer matching algorithm and a dataset relating a response to a profile can be used to determine the preference profile of the user. In another embodiment, a collaborative filtering model trained on ratings of products and the user's ratings of skincare products is used to assign the user to a preference profile.

Figure 7:
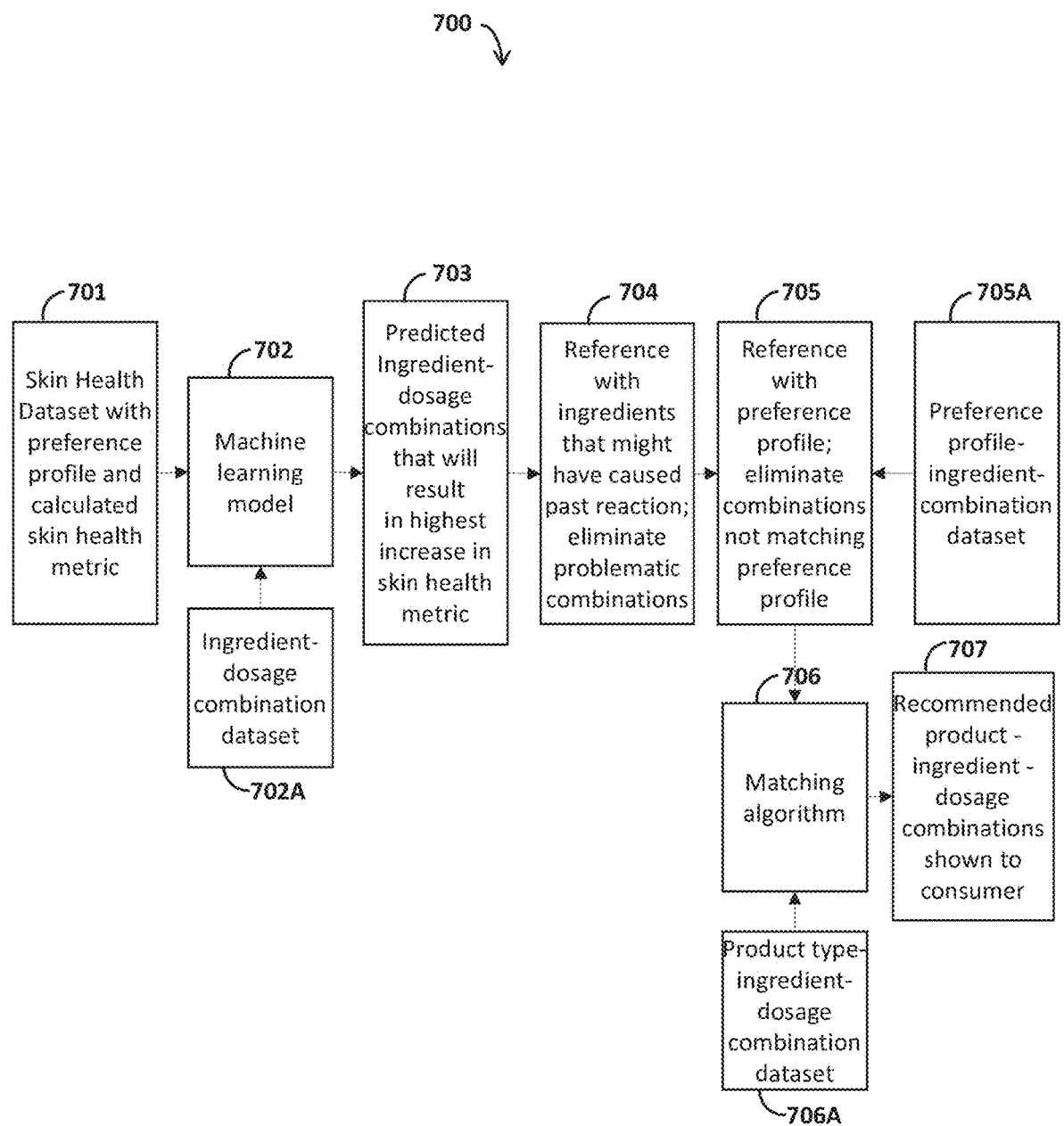
FIG. 7 is a schematic diagram illustrating a computerized skin care formulation design process, according to an illustrative embodiment of the invention.

FIG. 7 is a schematic diagram 700 illustrating a computerized skincare formulation design process, according to an illustrative embodiment of the invention. The method can be implemented on a computing device, e.g., the server computing device 104 shown and described above in FIG. 1. In a first step 701, a skin health data set is used to assign the user to a preference profile and calculate a skin health metric. In a second step 702, the skin health metric and the skin health dataset are provided to a machine learning model e.g., an ensemble of GRU or LSTM recurrent neural network and optimization algorithms, and is cross-referenced with an ingredient-dosage combination data set 702A. In a third step 703, the machine learning model outputs one or more predicted ingredient-dosage combinations, e.g., ones that will result in the highest, or one of the highest, increases in the skin health metric. In a fourth step 704, referencing the skin health data set and the field with potential ingredients that could have caused a reaction in the past, a computing device eliminates potential ingredient-dosage combinations with those ingredients. In a fifth step 705, the computing device employs a matching algorithm, cross-referencing with a preference profile-ingredient combination data set 705A. In a sixth step 706, the computing device employs a matching algorithm, cross-referencing with a product type-ingredient-dosage combination data set 706A. In a seventh step 707, the computing device generates one or more product-ingredient-dosage combinations for providing to the user.

Figure 8:
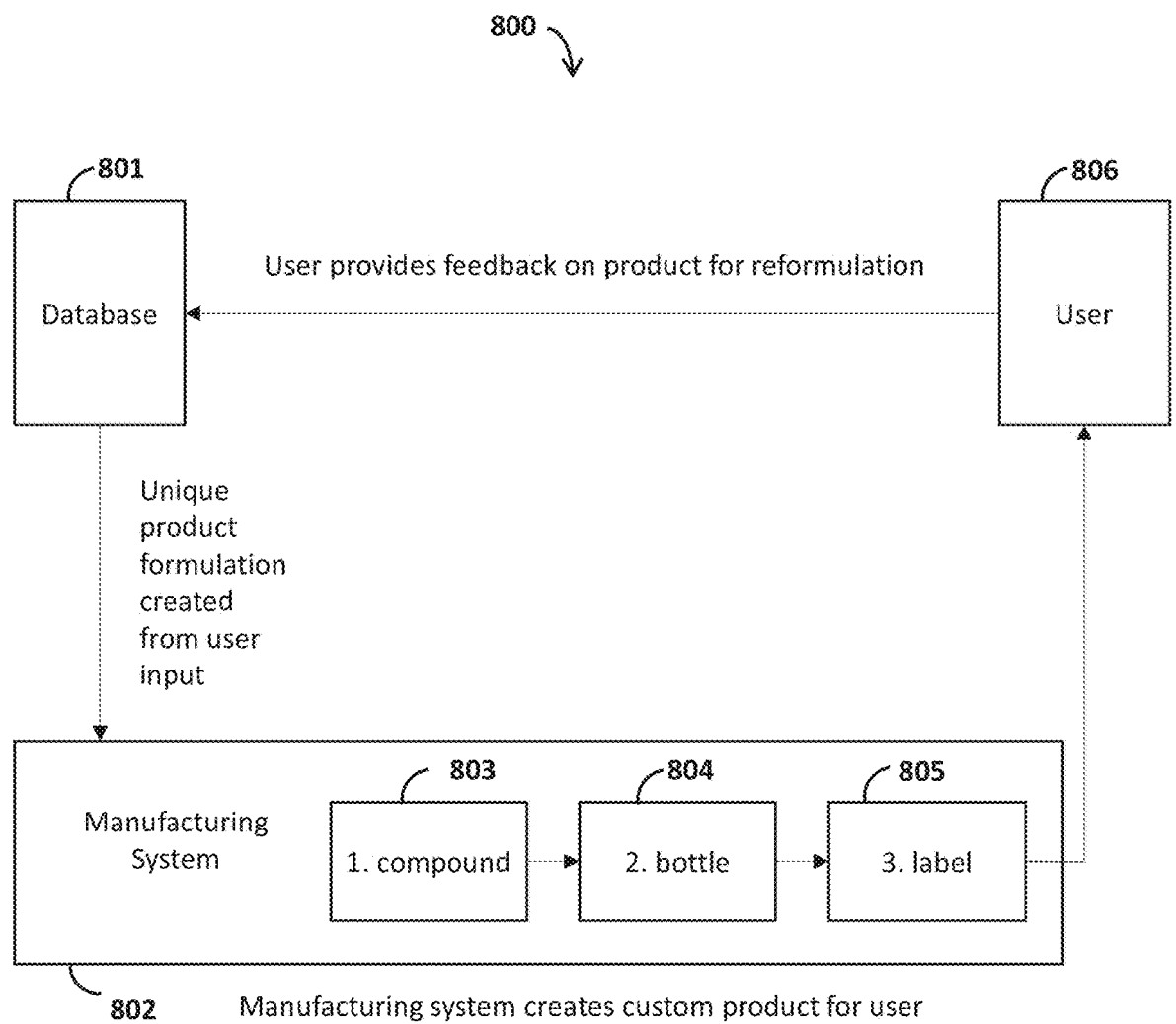
FIG. 8 is a schematic diagram illustrating a method of manufacturing a personalized skin care product for a user, according to an illustrative embodiment of the invention.

FIG. 8 is a schematic diagram 800 illustrating a method of manufacturing a personalized skin care product for a user, according to an illustrative embodiment of the invention. A database 801 provides to a manufacturing system 802 a product formulation having a unique skin identifier for the user and based on a unique skin health data set of the user. In a first manufacturing system step 803, the manufacturing system 802 compounds a customized skincare product according to the product formulation. In a second manufacturing system step 804, the manufacturing system 802 bottles the customized skincare product. In a third manufacturing system step 805, the manufacturing system 802 labels the container with a label displaying the at least one ingredient. The product is then provided to the user 806 for use. In some embodiments, as described above, the user 806 can provide feedback on the product for reformulation.

Figure 9C:

FIGS. 9A-9C are screen shots 901, 902, 903 of a user questionnaire eliciting certain dermal data, according to an illustrative embodiment of the invention. As shown, screen shot 901 elicits information about a user's goals (e.g., "Learning more about my skin"; "Tracking my skin progress"; "Achieving my skin goals"; and "A personalized formula") and skin concerns (e.g., "Acne", "Congestion/Blackheads", "Discoloration/Spots", "Dryness", "Redness/Irritation", "Sum Damage", and "Wrinkles/Fine Lines"). Screen shot 902 elicits information regarding a user's most important skin concerns, current products, favorite products, and disfavored products. Screen shot 903 elicits information regarding a user's skin sensitivity, skin sensitivity to the sun, and overall happiness with the user's skin. These variables can be in the skin health dataset and can be incorporated as factors to account for in the machine learning algorithms that predict what ingredient-dosage will be most effective in increasing the skin health metric of the user.

FIG. 10 is a screen shot 1000 of a skin care product recommendation, according to an illustrative embodiment of the invention. The screen shot 1000 shows a skin care product having a carrier of Jojoba and active ingredients of Calendula and Echium. The screen shot 1000 also displays a more detailed breakdown of the formulation, for example stating properties of Jojoba, Calendula and Echium for the user's reference and tags showing the user with which condition or goal the carrier or active ingredient may be associated. This screen helps the user understand how the skin health data collected relates to their recommended product-ingredient-dosage combinations by highlighting the benefits of the combination for the user's specific skin condition and skin concerns.

In some embodiments, one or more user input variables can be automatically determined and inputted into the algorithms described herein via another application or plug-in installed on the user computing device. For example, data involving genetics, diet, sleep quality, stress levels, and/or time sent in front of electronic screens may be provided by integration with another application installed on the device. For example, genetic data can be collected from DNA analysis services. The user's current diet, including dietary allergies, and changes in diet can be collected by manual input or from diet tracking applications already being used. Sleep habits and quality can be collected from wearable technologies that the user already uses. The data captured can include sleep quality, hours of sleep, and/or resting heart rate when sleeping. A computer algorithm can calculate average and variance levels for each of these data points from the prior thirty days. Stress levels can be captured from the same wearable technologies and data captured can include heart rate. A computer algorithm can calculate an average and a variance from, e.g., the prior thirty days.

In another example, time in front of screens can be captured by the user's cellular device. A matching algorithm can categorize the average hours spent each day over the past thirty days into buckets, e.g., High, Medium, and Low. In some embodiments, user input of current skin care products used is matched to an official product name using a skincare product database, e.g., by manual or bar code. In some embodiments, user selection of sample ingredient in an analysis process is matched to an absorption and feel preference profile. In any event, many of the variables (e.g., those falling under "Personal History", "Lifestyle", and/or "Skin History" groupings as shown in FIG. 6) can be ascertained, at a minimum, via answers to intake survey questions self-reported by users. All of these data points can be included in the first skin health data set and are factors that the machine learning models (e.g., a deep learning framework) use to predict which ingredient-dosage combinations would be most effective in increasing the user's skin health metric(s).

In some embodiments, calculating formulation instructions for manufacturing a first skincare product by a formulation specialist or machine includes calculating, based on issues found from skin image analysis, severity scores, oil and moisture indices, (i) a skin health metric based on a trained logistic regression model and a separate scorecard dataset (e.g., similar to what FICO does for one's credit score); and (ii) combining skin health metrics with prior inputs, using a trained machine learning model to predict the best product-ingredient-dosage combinations. A training data set can include a longitudinal data set of one or more skin health metrics, individual skin issues determinations, severity scores, oil and moisture indices, products-ingredient-dosage recommendation, and/or changes in composite score. In such a data set, a computer can calculate whether a change in composite score represents a statistically significant improvement or not (e.g., by making a binary decision). Possible calculation modes include, but are not limited to: a time-series, logistic model; a collaborative filtering model to predict complementary product-ingredient-dosage combinations; a neural network with loops.

In some embodiments, in which the data inputs further include information reflecting at least one of temperature, humidity, or environmental ultraviolet index of the user's location, the user can input his or her zip code during the intake process, and a computing device can input this zip code into a weather database and store in a temporary data set the temperature values, humidity values and UV Index, e.g., for each of the last thirty days. A computer algorithm can then calculate the average and variance of each of these variables. These figures can then be stored in the first skin health data set.

In some embodiments, in which the one or more data inputs include information reflecting at least one of a user-reported assessment of skin health, the user can provide a self-reported assessment of skin health (e.g., on a scale of 1 to 5). Where the user inputs include skincare product usage, in the intake process, the user can scan or type in the products they have used, and the computing device can match the product with complete product name in a separate product database. The user can identify in the intake process how many days a week he or she uses each product. The user can select from a pre-determined list his or her specific skin concerns. The user can type in a name of product or ingredient to which he or she has had a reaction, and it can be matched with a complete product name in a separate product database. A computer algorithm can identify the main active, preservative or potentially harmful ingredients from the product to which the user had a reaction. In some embodiments, the user identifies favorite products used in the past and provide data about absorption and texture preferences. The products currently used, frequency of use, favorite past products, absorption and texture preferences, and potential ingredients that may have caused prior reaction can be stored in the first skin health data set.

In some embodiments, in which the one or more data inputs include at least one elasticity measurement of the user's skin, an elasticity measurement device can be used (e.g., a frequency oscillation sensor and/or a suction pressure measurement device). The user can take indenture value measurements (e.g., in Newtons). These indenture values can be averaged and normalized to yield a normalized elasticity index. Where the data inputs include a pH of the skin, the pH can be measured using a litmus paper and/or an activation liquid. The normalized elasticity index and the pH value can be inputted into the first skin health dataset.

In some embodiments, referencing the skin health data set and the field with potential ingredients that could have caused a reaction in the past, a computer algorithm creates a rule not to include those ingredients in the formulations of products. Incorporating this rule, a computer algorithm predicts the ingredient-dosage combinations that will result in the highest increase in the user's skin health metric. In some embodiments, with inputs of first skin health data set and a data set of diet and lifestyle changes, a computer algorithm recommends specific diet and lifestyle habits that will increase the user's skin health metric. The computer algorithm leverages a machine learning model that has been trained on a longitudinal dataset including diet, lifestyle habits, skin concerns, severity scores and skin health metric. In some embodiments, in which a personalized skincare routine is generated that includes a recommendation for at least one of a cleanser, a serum, a facial oil, a moisturizer, dietary supplements, or a sunscreen, inputs of recommended ingredient-dosage combination and a product dataset of ingredient-dosages matched to product types, and a computer algorithm compares the recommended ingredient-dosage combinations for a user and pulls from the product dataset the associated product types suitable for the recommended ingredient-dosage combinations.

In some embodiments, the invention can be implemented in multiple settings, for example in a physical location or at home. In the physical location, the process can be guided through a kiosk or in-location device and follow the same process as described above. In addition, the user can receive their personalized product and personalized routine in the same visit as completing the analysis. In the at-home setup, the user can receive the personalized skincare product(s) via mail after completing the analysis.

Example Implementation

Subject A
Environmental+Background Data
Female, 27 years old, Asian, 5'5, 135 lbs, located in Boston, Mass.
No known allergies, no previous reactions to skin care products, uses daily sunscreen, regularly experiences dry and itchy skin, no recent experiences of acne
Frequent traveler, non-smoker, drinks 6 glasses of water a day, vegetarian, high stress level, exercises 2× a week
First diagnosis (fall) happening during the month of October.
Raw Visual+Physical Skin Data
Technique Measurement
Visible Imaging Identified dryness of skin on forehead and chin, discoloration on the forehead correlated with dry patches of skin, redness on forehead, wrinkles identified on forehead and around mouth, breakouts not a concern
Oil Measurements Forehead—15%, Nose—18%, Cheeks—21%
Moisture Measurements Forehead— 12%, Nose— 15%, Cheeks— 17%
Absorption Preference Identified "non-greasy" as preference, selected "absorbs quickly"
Transformed Skin Health Variables

| | |
|---|---|
| Oil Classification | 4 Index Score, Not Oily (average of 15%, 18%, 21% < threshold of 35%) |
| Moisture Classification | 3 Index Score, Dehydrated (average of 12%, 15%, 17% < threshold of 30%) |
| Discoloration Score | 40/100 |
| Redness Score | 50/100 |
| Wrinkles Score | 60/100 |

Figure 11:
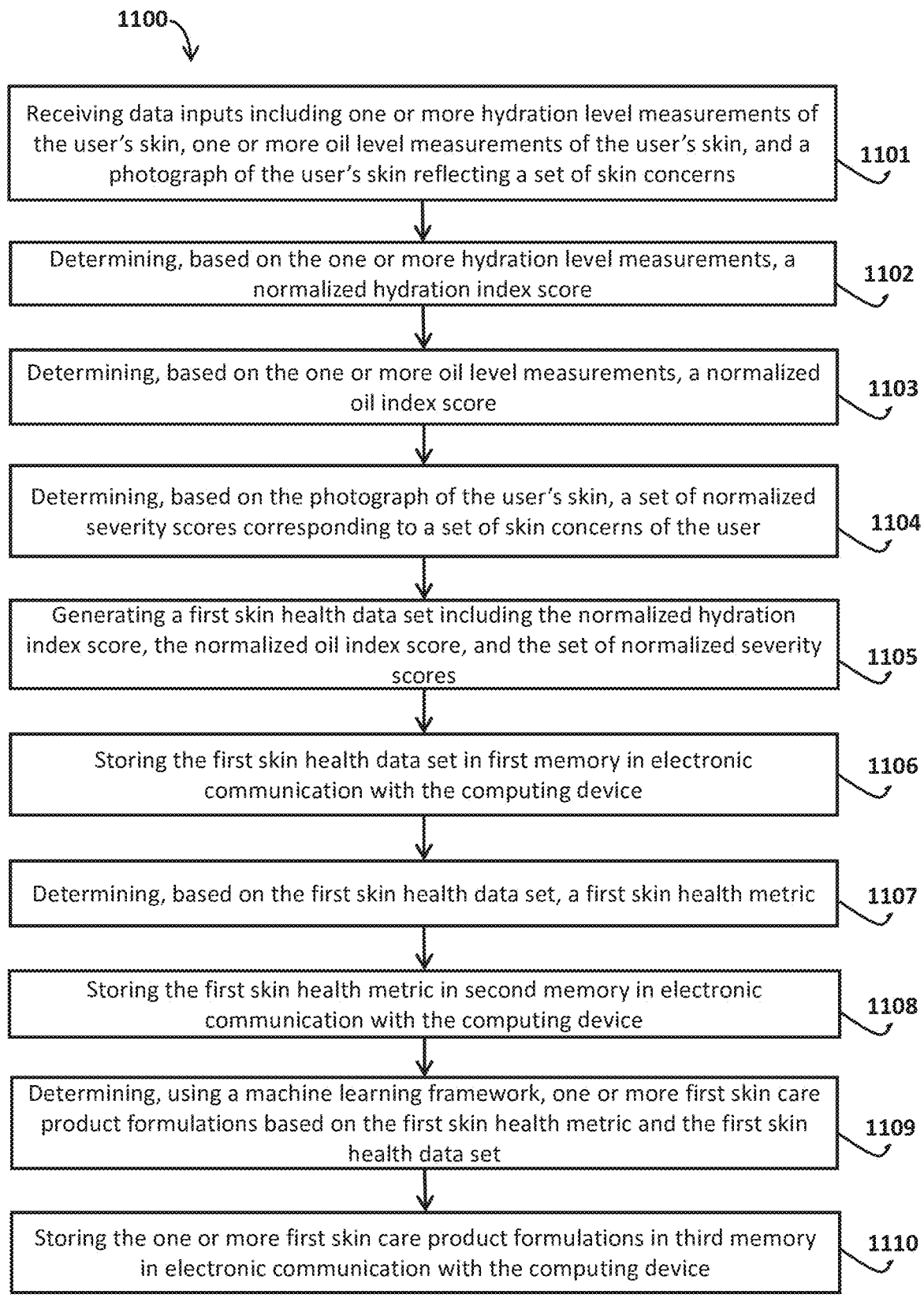
FIG. 11 is a flow chart of a computerized method of formulating a skin care product for a user, according to an illustrative embodiment of the invention.

Skin Health Metric: Breakouts (100)+Discoloration (40)+Redness (50)+Wrinkles (50)+Non-Smoking (100)+Water Intake (50)+High Stress (25)+Frequent Traveler (20)+Vegetarian (70)+Exercise (40)=545
Preference Profile: "Non-greasy" matched to Profile 3 ("Non-heavy, Moderate Base")
Ingredient-Dosage Matching
Potential Ingredients:
Potential Bases: Aqua (water), Rose water, Aloe Water, Evening Primrose, Squalane,
Potential Active Ingredients: Hyaluronic Acid, Ascorbic Acid (Vitamin C), Ascorbyl Glucoside
(Vitamin C derivative) Niacinamide, Retinol
Potential Conflicts (eliminating use of both): Niacinamide and Ascorbic Acid (used together create Niacin with side effect of redness and flushing)
Recommended Ingredient-Dosage Combinations:
Formulation (A-1): Aqua (water)+Ascorbyl Glucoside 8%
Formulation (A-2): Squalane+Hyaluronic Acid
Preference Profile Matching:
Formulation (A-1): Compatible with Preference Profile 3 ("Non-heavy, Moderate")
Formulation (A-2): Compatible with Preference Profile 3 ("Non-heavy, Moderate")
Product-Ingredient-Dosage Matching:
Products recommended for solving user's discoloration, redness, dryness: Morning serum (A-1), Night serum (A-2)
User Choice:
Formulation (A-1): User does not change recommended formulation and product recommendation FIG. 11 is a flow chart 1100 of a computerized method of formulating a skin care product for a user, according to an illustrative embodiment of the invention. The steps shown can be carried out by a computing device, e.g., the computing device 104 shown and described above in FIG. 1. In a first step 1101, data inputs are received including one or more hydration level measurements of the user's skin, one or more oil level measurements of the user's skin, and a photograph of the user's skin reflecting a set of skin concerns. In a second step 1102, a normalized hydration index score is determined based on the one or more hydration level measurements. In a third step 1103, a normalized oil index score is determined based on the one or more oil level measurements. In a fourth step 1104, a set of normalized severity scores corresponding to a set of skin concerns of the user is determined based on the photograph of the user's skin. In a fifth step 1105, a first skin health data set including the normalized hydration index score, the normalized oil index score, and the set of normalized severity scores is generated. In a sixth step 1106, the first skin health data set is stored in first memory in electronic communication with the computing device. In a seventh step 1107, a first skin health metric is determined based on the first skin health data set. In an eighth step 1108, the first skin health metric is stored in second memory in electronic communication with the computing device. In a ninth step 1109, one or more first skin care product formulations are determined, using a machine learning framework operating on the computing device, based on the first skin health metric and the first skin health data set. In a tenth step 1110, the one or more first skin care product formulations are stored in third memory in electronic communication with the computing device.

Figure 12:
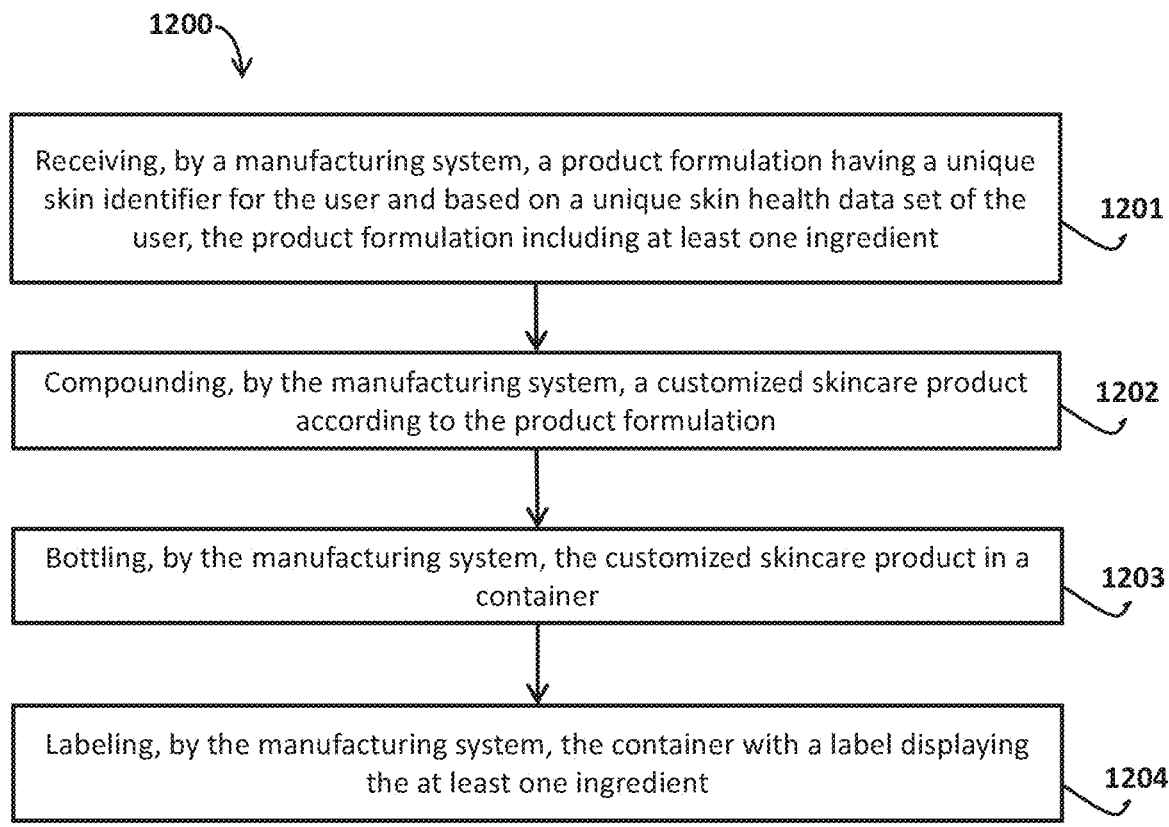
FIG. 12 is a flow chart of a method of manufacturing a skin care product for a user, according to an illustrative embodiment of the invention.

FIG. 12 is a flow chart 1200 of a method of manufacturing a skin care product for a user, according to an illustrative embodiment of the invention. The steps shown can be carried out by a manufacturing system, e.g., an indoor manufacturing facility or another facility. In a first step 1201, a manufacturing system receives a product formulation (e.g., as generated according to one or more methods described herein) having a unique skin identifier for the user and based on a unique skin health data set of the user, the product formulation. In a second step 1202, the manufacturing system compounds a customized skincare product according to the product formulation. In a third step 1203, the manufacturing system bottles the customized skincare product in a container. In a fourth step 1204, the manufacturing system labels the container with a label displaying ingredients.

Figure 13:
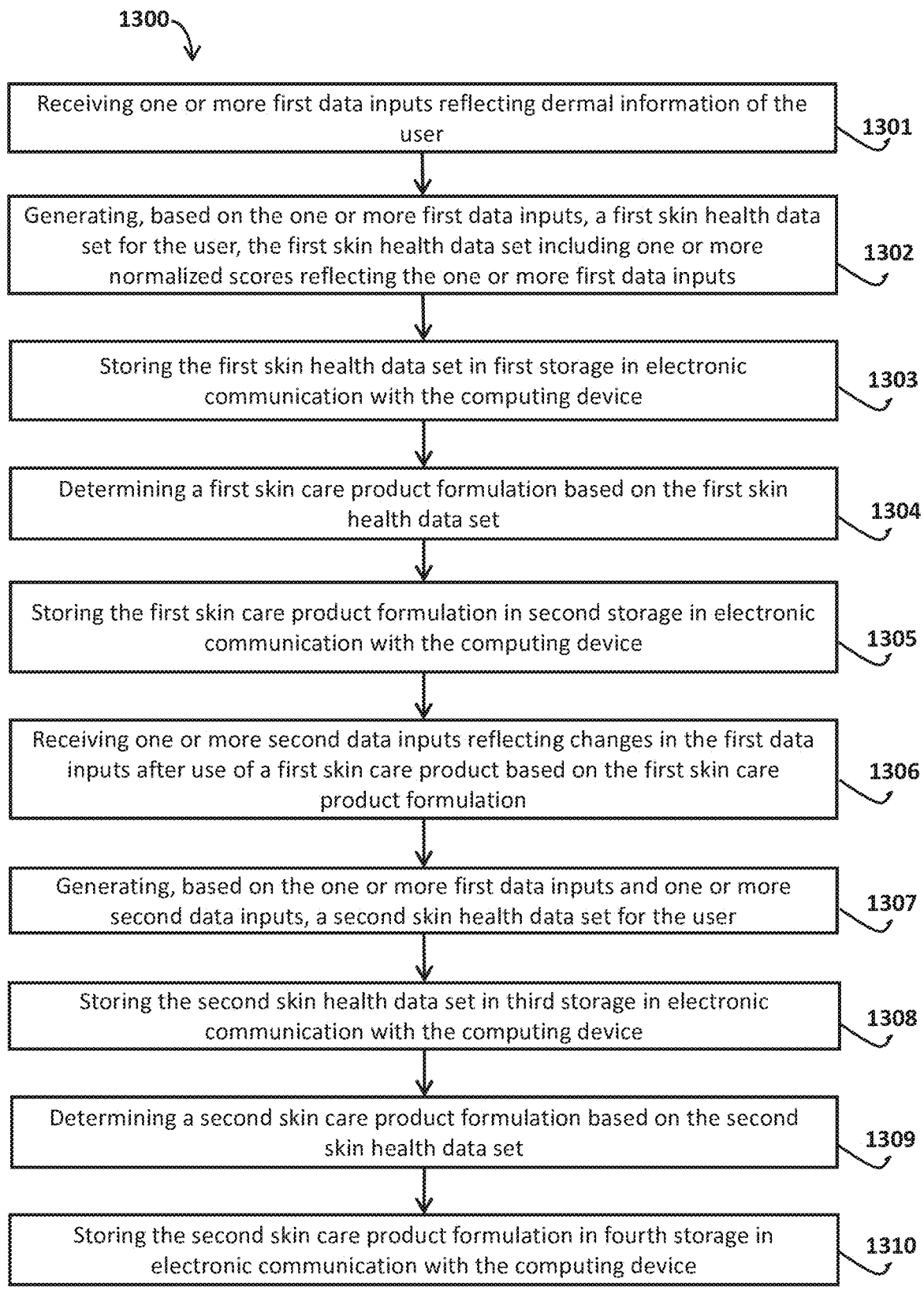
FIG. 13 is a flow chart of a computerized method of formulating first and second skin care product for a user, according to an illustrative embodiment of the invention.

FIG. 13 is a flow chart 1300 of a computerized method of formulating first and second skin care product for a user, according to an illustrative embodiment of the invention. The steps shown can be carried out by a computing device, e.g., the computing device 104 shown and described above in FIG. 1. In a first step 1301, one or more first data inputs are received reflecting dermal information of the user. In a second step 1302, a first skin health data set is generated for the user based on the one or more first data inputs, the first skin health data set including one or more normalized scores reflecting the one or more first data inputs. In a third step 1303, the first skin health data set is stored in first storage in electronic communication with the computing device. In a fourth step 1304, a first skincare product formulation is determined based on the first skin health data set. In a fifth step 1305, the first skincare product formulation is stored in second storage in electronic communication with the computing device. In a sixth step 1306, one or more second data inputs are received reflecting changes in the first data inputs after use of a first skincare product based on the first skin care product formulation. In a seventh step 1307, a second skin health data set for the user is generated based on the one or more first data inputs and one or more second data inputs. In an eighth step 1308, the second skin health data set is stored in third storage in electronic communication with the computing device. In a ninth step 1309, a second skincare product formulation is determined based on the second skin health data set. In a tenth step 1310, the second skincare product formulation is stored in fourth storage in electronic communication with the computing device.

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a programmable processor, a computer, and/or multiple computers. The computer program can be deployed in a cloud computing environment (e.g., Amazon® AWS, Google Cloud Platform, Microsoft® Azure, etc.). Method steps can be performed by one or more processors executing a computer program to perform functions of the invention by operating on input data and/or generating output data.

To provide for interaction with a user, the above described techniques can be implemented on a computing device in communication with a display device, e.g., a plasma or LCD (liquid crystal display) monitor or a mobile computing device display or screen for displaying information to the user and a keyboard and a pointing device, e.g., a mouse, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above-described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be interconnected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, near field communications (NFC) network, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

Information transfer over transmission medium can be based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, Universal Mobile Telecommunications System (UMTS), 3GPP Long Term Evolution (LTE) and/or other communication protocols.

Devices of the computing system can include, for example, a computer, a computer with a browser device, a telephone, an IP phone, a mobile computing device (e.g., cellular phone, personal digital assistant (PDA) device, smart phone, tablet, laptop computer, electronic mail device), and/or other communication devices. The browser device includes, for example, a computer (e.g., desktop computer and/or laptop computer) with a World Wide Web browser (e.g., Chrome™ from Google, Inc., Microsoft® Internet Explorer® available from Microsoft Corporation, and/or Mozilla® Firefox available from Mozilla Corporation). Mobile computing device include, for example, a Blackberry® from Research in Motion, an iPhone® from Apple Corporation, and/or an Android™-based device. IP phones include, for example, a Cisco® Unified IP Phone 7985G and/or a Cisco® Unified Wireless Phone 7920 available from Cisco Systems, Inc.

It should also be understood that various aspects and embodiments of the invention can be combined in various ways. Based on the teachings of this specification, a person of ordinary skill in the art can readily determine how to combine these various embodiments. In addition, modifications may occur to those skilled in the art upon reading the specification.

What is claimed is:

1. A computerized method of formulating skin care products for a user using a plurality of machine learning models implemented on a computing device, the method comprising:
   receiving, by the computing device, one or more data inputs reflecting dermal information of the user after use of a first skincare product, the one or more data inputs including one or more hydration level measurements of the user's skin taken using a corneocyte test, one or more oil level measurements of the user's skin taken using a sebum test, and a photograph of the user's skin taken using a camera;
   determining, by the computing device, based on the one or more hydration level measurements, a normalized hydration index score using a first machine learning model trained on a data set of corneocyte test results;
   determining, by the computing device, based on the one or more oil level measurements, a normalized oil index score using a second machine learning model trained on a data set of sebum test results;
   generating, by the computing device, a plurality of transformed photographs of the user's skin based upon the photograph by applying one or more illumination adjustments to the photograph, creating a plurality of copies of the illumination-adjusted photograph, dividing each copy of the illumination-adjusted photograph into regions using a region map, and applying a different transformation to each copy of the illumination-adjusted photograph;
   determining, by the computing device, based on the plurality of transformed photographs of the user's skin, a set of normalized severity scores corresponding to a set of skin concerns of the user by applying a third machine learning model comprising a trained anomaly detection model or a trained convolutional neural network to each of the plurality of transformed photographs;
   generating, by the computing device, a skin health data set for the user, the first skin health data set including the set of normalized severity scores, the normalized hydration index score, and the normalized oil index score;
   storing, by the computing device, the skin health data set in first storage in electronic communication with the computing device;
   determining, by the computing device, a skincare product formulation based on the skin health data set;
   storing, by the computing device, the skincare product formulation in second storage in electronic communication with the computing device; and
   providing, by the computing device, the skincare product formulation to the user in the form of a recommendation.

2. The method of claim 1 wherein the first data inputs include information reflecting at least one of temperature, humidity, or environmental ultraviolet index of the user's location.

3. The method of claim 1 wherein the first data inputs include information reflecting at least one of user genetics, medical history, diet, water intake, smoking habits, known allergies, alcohol habits, sleep quality, stress levels, time spent in front of electronic screens, or sun exposure.

4. The method of claim 1 wherein the first data inputs include information reflecting at least one of a user-reported assessment of skin health, skin care product usage, past skin care product usage, past skin reactions, skin care goals, skin care concerns, skin care absorption or texture preferences.

5. The method of claim 1 wherein the first data inputs include at least one of an elasticity measurement of the user's skin, a wrinkle measurement of the user's skin, or a surface pH level of the user's skin.

6. A computing system for formulating a skincare product for a user using a plurality of machine learning models implemented on a computing device, the system comprising the computing device, configured to:
   receive one or more data inputs reflecting dermal information of the user after use of a first skincare product, the one or more data inputs including one or more hydration level measurements of the user's skin taken using a corneocyte test, one or more oil level measurements of the user's skin taken using a sebum test, and a photograph of the user's skin taken using a camera;
   determine, based on the one or more hydration level measurements, a normalized hydration index score using a first machine learning model trained on a data set of corneocyte test results;
   determine, based on the one or more oil level measurements, a normalized oil index score using a second machine learning model trained on a data set of sebum test results;
   generate a plurality of transformed photographs of the user's skin based upon the photograph by applying one or more illumination adjustments to the photograph, creating a plurality of copies of the illumination-adjusted photograph, dividing each copy of the illumination-adjusted photograph into regions using a region map, and applying a different transformation to each copy of the illumination-adjusted photograph;
   determine, based on the plurality of transformed photographs of the user's skin, a set of normalized severity scores corresponding to a set of skin concerns of the user by applying a third machine learning model comprising a trained anomaly detection model or a trained convolutional neural network to each of the plurality of transformed photographs;
   generate, a skin health data set for the user, the first skin health data set including the set of normalized severity scores, the normalized hydration index score, and the normalized oil index score;
   store the skin health data set in first storage in electronic communication with the computing device;
   determine a skincare product formulation based on the skin health data set;
   store the skincare product formulation in second storage in electronic communication with the computing device; and provide the skincare product formulation to the user in the form of a recommendation.

7. The system of claim 6, further including a user computing device in electronic communication with the computing device, wherein the user computing device is configured to collect and provide the data inputs to the computing device.

8. The method of claim 1, wherein determining a skincare product formulation based on the skin health data set comprises:
   determining, by the computing device, a skin health metric of the user associated with the skin health data set;
   determining, by the computing device, one or more ingredient-dosage combinations for the user by applying a fourth machine learning model, trained on an ingredient-dosage combination data set, to the skin health metric and the skin health data set;
   and determining, by the computing device, the skincare product formulation based upon the one or more ingredient-dosage combinations.

9. The method of claim 1, wherein the different transformations of the photograph comprise illumination adjustment, conversion to grayscale, application of an image filter, color space transformation, or any combination thereof.

10. The method of claim 9, wherein different transformations are applied to different regions of each transformed photograph.

11. The system of claim 6, wherein determining a skincare product formulation based on the skin health data set comprises:
    determining, by the computing device, a skin health metric of the user associated with the skin health data set;
    determining, by the computing device, one or more ingredient-dosage combinations for the user by applying a fourth machine learning model, trained on an ingredient-dosage combination data set, to the skin health metric and the skin health data set; and
    determining, by the computing device, the skincare product formulation based upon the one or more ingredient-dosage combinations.

12. The system of claim 6, wherein the different transformations of the photograph comprise illumination adjustment, conversion to grayscale, application of an image filter, color space transformation, or any combination thereof.

13. The system of claim 12, wherein different transformations are applied to the different regions of each transformed photograph.

\* \* \* \* \*